United States Patent [19]

Anton et al.

[11] Patent Number: 5,262,314
[45] Date of Patent: Nov. 16, 1993

[54] ENZYMATIC OXIDATION OF GLYCOLIC ACID IN THE PRESENCE OF NON-ENZYMATIC CATALYST FOR DECOMPOSING HYDROGEN PEROXIDE

[75] Inventors: David L. Anton; Anthony J. Arduengo, III; Robert DiCosimo, all of Wilmington, Del.

[73] Assignee: E. I. Du Pont de Nemours and Company, Wilmington, Del.

[21] Appl. No.: 755,925

[22] Filed: Sep. 6, 1991

[51] Int. Cl.$^5$ .................. C12P 7/40; C07C 51/16
[52] U.S. Cl. ..................... 435/136; 562/538
[58] Field of Search .................. 562/538; 435/136

[56] References Cited

U.S. PATENT DOCUMENTS

| | | | |
|---|---|---|---|
| 3,281,460 | 10/1966 | Gandon | 260/530 |
| 4,094,928 | 6/1978 | Gaertner et al. | 260/944 |
| 4,146,731 | 3/1979 | Ogahara et al. | 562/531 |
| 4,233,452 | 11/1980 | Williams et al. | 549/79 |
| 4,235,684 | 11/1980 | Harada et al. | 204/79 |
| 4,455,371 | 6/1984 | Richardson et al. | 435/25 |
| 4,670,191 | 6/1987 | Kleiner et al. | 260/502.5 F |
| 4,851,159 | 7/1989 | Fields et al. | 562/17 |
| 4,871,669 | 10/1989 | Murray et al. | 435/147 |
| 4,909,999 | 3/1990 | Cummings et al. | 422/298 |

FOREIGN PATENT DOCUMENTS 0186648 12/1985 European Pat. Off.
0413672 2/1991 European Pat. Off.

OTHER PUBLICATIONS

Tolbert et al, J. of Biol. Chem., 181, 2001–2009, 1949.
Zelitch et al., J. Biol. Chem., 201, 707–718, 1953.
Tolbert et al., "J. Biool. Chem." vol. 181, pp. 905–914 (1949).
Richarson et al., "J. Biol. Chem." vol. 236 pp. 1280–1284 (1961).
Clagette et al., "J. Biol. Chem.", vol. 178 pp. 977–987 (1961).
Zelitch et al., "J. Biol. Chem." vol. 201 pp. 707–718 (1953).
Robinson et al, "J. Biol. Chem.," vol. 237, pp. 2001–2009 (1962).
Frigerio et al., "J. Biol. Chem.," vol. 231 pp. 135–157 (1958).
Zelitch et al., "Methods in Enzymology" vol. 1 pp. 528–532 (1955).
Nishimura et al., "Arch. Biochem. Biophys." vol. 222 pp. 397–402 (1983).
Asker et al., "Biochim Biophys. Acta." vol. 761 pp. 103–108 (1983).
Emes et al., "Int. J. Biochem.", vol. 16 1373–1378 (1984).
Cederlund et al., "Eur. J. Biochem." vol. 173 pp. 523–530 (1988).
Lindquist et al., "J. Biol. Chem." vol. 264 pp. 3624–3628 (1989).
Yagai, "Methods of Biochemical Analygis," vol. X pp. 319–355 (1962).
Volokito et al., "J. Biol. Chem." vol. 262, 15825 (1987).
Macheroux et al., "Biochemistry", vol. 30 pp. 4612–4619 (1991).
D. Scott, "Enzymologia" vol. 22 pp. 223–228 (1960).
Vasudevan and Weiland, "Biotechnology and Bioengineering" vol. 36 pp. 783–789 (1990).
Altomare et al., "Biotechnology and Bioengineering" vol. 16 pp. 1659–1673 (1974) and 1675–1680 (1974).
Tarhan and Uslan, "Process Biochem" Feb. 1990, pp. 14–18.

*Primary Examiner*—Marianne M. Cintins
*Assistant Examiner*—Rebecca Cook

[57] ABSTRACT

A process for the production of glyoxylic acid by reacting glycolic acid and oxygen in an aqueous solution at pH 7–10 in the presence of the enzyme glycolate oxidase and a non-enzymatic catalyst for the decomposition of hydrogen peroxide, and an amine buffer capable of forming a chemical adduct with glyoxylic acid.

21 Claims, No Drawings

ENZYMATIC OXIDATION OF GLYCOLIC ACID IN THE PRESENCE OF NON-ENZYMATIC CATALYST FOR DECOMPOSING HYDROGEN PEROXIDE

BACKGROUND OF THE INVENTION

1. Field of the Invention

This invention relates to an improved process for the production of glyoxylic acid by the use of a combination of enzymatic and non-enzymatic catalyzed oxidation of glycolic acid. More specifically, the present invention relates to the use of glycolate oxidase and a non-enzymatic catalyst for the decomposition of hydrogen peroxide.

2. Description of the Related Art

Glycolate oxidase, an enzyme commonly found in leafy green plants and mammalian cells, catalyzes the oxidation of glycolic acid to glyoxylic acid, with the concomitant production of hydrogen peroxide. N. E. Tolbert et al., *J. Biol. Chem.*, Vol. 181, 905–914 (1949) first reported an enzyme, extracted from tobacco leaves, which catalyzed the oxidation of glycolic acid to formic acid and $CO_2$ via the intermediate formation of glyoxylic acid. The addition of certain compounds, such as ethylene diamine, limited the further oxidation of the intermediate glyoxylic acid. The oxidations were carried out at a pH of about 8, typically using glycolic acid concentrations of about 3–40 mM (millimolar). The optimum pH for the glycolate oxidation was reported to be 8.9. Oxalic acid (100 mM) was reported to inhibit the catalytic action of the glycolate oxidase. Similarly, K. E. Richardson and N. E. Tolbert, *J. Biol. Chem.*, Vol. 236, 1280–1284 (1961) showed that buffers containing tris(hydroxymethyl)aminomethane inhibited the formation of oxalic acid in the glycolate oxidase catalyzed oxidation of glycolic acid. C. O. Clagett, N. E. Tolbert and R. H. Burris, *J. Biol. Chem.*, Vol. 178, 977–987 (1949) reported that the optimum pH for the glycolate oxidase catalyzed oxidation of glycolic acid with oxygen was about 7.8–8.6, and the optimum temperature was 35°–40° C.

I. Zelitch and S. Ochoa, *J. Biol. Chem.*, Vol. 201, 707–718 (1953), and J. C. Robinson et al., *J. Biol. Chem.*, Vol. 237, 2001–2009 (1962), reported that the formation of formic acid and $CO_2$ in the spinach glycolate oxidase-catalyzed oxidation of glycolic acid resulted from the non-enzymatic reaction of $H_2O_2$ with glyoxylic acid. They observed that addition of catalase, an enzyme that catalyzes the decomposition of $H_2O_2$, greatly improved the yields of glyoxylic acid by suppressing the formation of formic acid and $CO_2$. The addition of FMN (flavin mononucleotide) was also found to increase the stability of the glycolate oxidase.

N. A. Frigerio and H. A. Harbury, *J. Biol. Chem.*, Vol. 231, 135–157 (1958) have reported on the preparation and properties of glycolic acid oxidase isolated from spinach. The purified enzyme was found to be very unstable in solution; this instability was ascribed to the relatively weak binding of flavin mononucleotide (FMN) to the enzyme active site, and to the dissociation of enzymatically active tetramers and/or octamers of the enzyme to enzymatically-inactive monomers and dimers, which irreversibly aggregate and precipitate. The addition of FMN (flavin mononucleotide) to solutions of the enzyme greatly increased its stability, and high protein concentrations or high ionic strength maintained the enzyme as octamers or tetramers.

There are numerous other references to the oxidation of glycolic acid catalyzed by glycolic acid oxidase, for example:

Isolation of the Enzyme
(usually includes an assay method):

I. Zelitch in *Methods of Enzymology*, Vol. 1, Academic Press, New York, 1955, p. 528–532, from spinach and tobacco leaves.

M. Nishimura et al., *Arch. Biochem. Biophys.*, Vol. 222, 397–402 (1983), from pumpkin cotyledons.

H. Asker and D. Davies, *Biochim. Biophys. Acta*, Vol. 761, 103–108 (1983), from rat liver.

M. J. Emes and K. H. Erismann, *Int. J. Biochem.*, Vol 16, 1373–1378 (1984), from Lemna Minor L.

Structure of the enzyme:

E. Cederlund et al., *Eur. J. Biochem.*, Vol. 173, 523–530 (1988).

Y. Lindquist and C. Branden, *J. Biol. Chem.*, Vol. 264, 3624–3628, (1989).

SUMMARY OF THE INVENTION

This invention relates to a process for the production of glyoxylic acid (OCHCOOH) where glycolic acid ($HOCH_2COOH$) (200 to about 2500 mM) and oxygen are reacted in an aqueous solution (pH 7 to 10) in the presence of two catalysts: the enzyme glycolate oxidase ((S)-2-hydroxy-acid oxidase, EC 1.1.3.15), and a non-enzymatic catalyst which decomposes hydrogen peroxide. Under optimum conditions, significant improvements in the yields of glyoxylic acid are obtained at high conversion of glycolic acid, compared to reactions run in the absence of a catalyst which decomposes hydrogen peroxide.

Thus the present invention provides a process for the production of glyoxylic acid comprising contacting, in aqueous solution, at a pH of about 7 to about 10 and a temperature of about 0° to about 40′ C., glycolic acid, glycolate oxidase, and oxygen and from 25 to 100,000 IU/mL of a non-enzymatic catalyst for decomposing hydrogen peroxide wherein the initial concentration of glycolic acid is 200 mM to about 2500 mM and of glycolate oxidase is 0.01 to 100 IU/mL, wherein the ratio, as measured in IU/mL, for each of peroxide-decomposing catalyst to glycolate oxidase is at least about 250:1, and an amine buffer capable of forming a chemical adduct with glyoxylic acid where the initial molar ratio of amine to glycolic acid is within the range of from 1.0 to 3.0.

DESCRIPTION OF THE PREFERRED EMBODIMENTS

This invention describes the use of a combination of enzymatic and non-enzymatic catalysts for the manufacture of glyoxylic acid from glycolic acid (hydroxyacetic acid). Although the enzyme-catalyzed oxidation of glycolic acid has been known for many years, high selectivities to glyoxylic acid have not been previously obtained, nor has the oxidation of glycolic acid been performed at concentrations of 0.20M to 2.5M. A previous, commonly assigned, application, U.S. Ser. No. 07/422,011 filed Oct. 16, 1989, "Production of Glyoxylic Acid from Glycolic Acid", described a process for the enzymatic conversion of glycolic acid to glyoxylic acid in the presence of oxygen, an amine buffer, and the soluble enzymes glycolate oxidase and catalase. This process demonstrated the unexpected synergistic effect of using both catalase (to destroy by-product hydrogen peroxide) and an amine buffer capable of forming a chemical adduct with the glyoxylic acid produced (limiting its further oxidation) and is herein incorporated by reference for such purpose. Neither the separate addition of catalase or an amine buffer were found to produce the high selectivity observed when both were present, and the almost quantitative yields of glyoxylic acid obtained were more than expected from a simple additive effect of using catalase or amine buffer alone. An alternate method of performing this reaction, which substitutes for the enzyme previously employed an inorganic or organic compound capable of destroying hydrogen peroxide, has now been developed.

In two related patent applications, the above-mentioned U.S. Ser. No. 07/422,011, filed October, 1989, Ser. No. 07/755,926, filed on even date herewith, processes for the production of glyoxylic acid are described which employ soluble and immobilized catalase, respectively, as a catalyst for the destruction of the by-product hydrogen peroxide generated during the reaction. The major advantages for using catalase, instead of one of the many non-enzymatic catalysts capable of decomposing hydrogen peroxide, is that:

(1) catalase has a specific catalytic activity (catalytic activity per weight of catalyst) ten to one hundred times that of a comparable non-enzymatic catalyst, and (2) catalase does not catalyze the oxidation of glycolic acid or glyoxylic acid by hydrogen peroxide, thus making the essentially quantitative conversion of glycolic acid to glyoxylic acid possible.

Several disadvantages also exist for the use of catalase instead of a non-enzymatic catalyst. D. Scott, *Enzymologia*, Vol. 22, 223–228 (1960), and P. T. Vasudevan and R. H. Weiland, *Biotechnology and Bioengineering*, Vol. 36, 783–789 (1990), report that catalase is deactivated (loses its catalytic activity) by hydrogen peroxide as it decomposes hydrogen peroxide to water and oxygen; a similar deactivation of immobilized catalases has been described by R. E. Altomare et al., *Biotechnology and Bioengineering*, Vol. 16, 1659–1673 (1974) and 1675–1680 (1974), and by L. Tarhan and A. H. Uslan, *Process Biochemistry*, February, 1990, pp. 14–18. This rate of deactivation is fairly rapid when compared to the long catalyst lifetimes observed for similar non-enzymatic catalysts.

A second disadvantage of using the catalase enzyme is that it is relatively expensive when compared to non-enzymatic catalysts with similar activity. Also, the preferred form of the enzyme catalyst is as an immobilized enzyme, which results in a yield loss of enzyme activity when the enzyme is immobilized, as well as an added cost for immobilization on a support. The substitution of an organic or inorganic non-enzymatic catalyst for catalase could significantly lower the catalyst cost for this process.

It is generally well known to those skilled in the art that a wide variety of inorganic and organic catalysts exist for the catalytic decomposition of hydrogen peroxide. A list of the possible choices of catalyst would include, but is not limited to, unsupported manganese(IV) oxide, manganese(IV) oxide on carbon, ruthenium metal on alumina, ruthenium metal powder, ruthenium metal on carbon, platinum oxide, platinum black, platinum on alumina, palladium black, palladium on alumina, copper(II) oxide, lead on alumina, soluble salts or chelates of Mn(II), Mn(IV), Cu(II), Ni(II), Co(II), Zn(II), Fe(II), Fe(III), and Cr(III), and organic compounds such as activated carbon or N,N'-di(lower alkyl or hydroxyalkyl) substituted imidazole-2-thiones. The Examples list the results obtained for the oxidation of glycolate to glyoxylate with the individual substitution of a number of the compounds in the preceding list for catalase. Significant increases in the yields of glyoxylic acid are obtained in comparison to oxidations performed in the absence of catalase or a catalyst which decomposes hydrogen peroxide.

Examination of the Examples which describe the use of inorganic or organic catalysts for the decomposition of hydrogen peroxide will reveal that mass balances of less than 100% are sometimes observed, depending on the catalyst; this occurrence is at least in part due to the ability of some of these catalysts to catalyze the further oxidation (by oxygen, or by the hydrogen peroxide produced during the reaction) of the product glyoxylic acid to formate, and subsequently, the further oxidation of formate to carbon dioxide (see Example 14). The extent of this overoxidation is dependent on the choice of reaction conditions and concentration of catalyst, as well as on the catalyst itself. The glycolic acid starting material appears to be relatively insensitive to oxidation catalyzed by these catalysts (Example 13).

The following paragraphs describe the reaction conditions employed for the glycolate oxidase-catalyzed oxidation of glycolic acid to glyoxylic acid using inorganic or organic catalysts for the decomposition of hydrogen peroxide.

The glycolate oxidase used in the reaction should be present in an effective concentration, usually a concentration of 0.01 to 100 IU/mL, preferably about 0.1 to about 4 IU/mL. An IU (International Unit) is defined as the amount of enzyme (or catalyst) that will catalyze the transformation of one micromole of substrate per minute. A procedure for the assay of this enzyme is found in I. Zelitch and S. Ochoa, *J. Biol. Chem.*, Vol. 201, 707–718 (1953). This method is also used to assay the activity of recovered or recycled glycolate oxidase.

The pH of the reaction solution should be between 7 and 10, preferably between 8.0 and 9.5. The pH can be maintained by a buffer, since enzyme activity varies with pH. The pH of the reaction decreases slightly as the reaction proceeds, so it is often useful to start the reaction near the high end of the maximum enzyme activity pH range, about 9.0–9.5, and allow it to drop during the reaction. As has been previously described in U.S. Ser. No. 07/422,011 filed Oct. 16, 1989, an amine buffer capable of complexing the glyoxylic acid (by forming an imine which is more stable to chemical or enzymatic oxidation) is employed together with a catalyst for the decomposition of hydrogen peroxide to maximize product selectivity. Ethylene diamine, or less preferably, tris(hydroxymethyl)methylamine (hereinafter TRIS), piperazine, or glyclyglycine improved the yield of glyoxylic acid. These amines are used in a molar ratio of amine/glycolic acid (starting amount) of 1.0 to 3.0, preferably 1.05 to 1.33. Within this range, the exact value may be adjusted to obtain the desired pH. With very basic amines used at high amine to glycolic acid ratios, it may be necessary to adjust the pH, as by adding acid, for example hydrochloric or sulfuric acids. With less basic amines such as TRIS, it may be necessary to add a base to maintain the desired pH.

The concentration of the catalyst having catalase-like activity (i.e. the ability to rapidly decompose hydrogen peroxide as it is produced) should be 25 to 100,000

IU/mL, preferably 350 to 14,000 IU/mL. It is preferred that the hydrogen peroxide-decomposing catalyst and glycolate oxidase concentrations be adjusted within the above ranges so that the ratio (measured in IU for each) of peroxide-decomposing catalyst to glycolate oxidase is at least about 250:1. Flavinmononucleotide (FMN) is an optional added ingredient, used at a concentration of 0.0 to 2.0 mM, preferably 0.01 to 0.2 mM.

The reaction rate is at least partially controlled by the rate at which oxygen can be dissolved into the aqueous medium. Oxygen can be added to the reaction as the oxygen in air, but it is preferred to use a relatively pure form of oxygen, and to use elevated pressures. Although no upper limit of oxygen pressure is known, oxygen pressures up to 50 atmospheres may be used, and an upper limit of 15 atmospheres is preferred. Sparging (bubbling) oxygen through the reaction mixture is optionally used with immobilized glycolate oxidase to maintain a high oxygen dissolution (and hence reaction) rate. Oxygen is sparged through the reaction mixture at a rate of 0.05 to 5 volumes of oxygen (measured at atmospheric pressure) per volume of reaction mixture per minute (vol/vol·min), and preferably between 0.2 and 2 vol/vol·min. Additionally, a convenient form of agitation is useful, such as stirring.

The reaction temperature is an important variable, in that it affects reaction rate and the stability of the enzymes. A reaction temperature of 0° C. to 40° C. may be used, but the preferred reaction temperature range is from 5° C. to 15° C. Operating in the preferred temperature range maximizes recovered enzyme activity at the end of the reaction.

Upon completion of the reaction and removal of the catalysts by filtration or centrifugation, the amine buffer is most conveniently removed by use of an ion exchange resin. Suitable acidic cationic exchange resins include "AMBERLITE" CG120 or "AMBERLITE" IR120 (Rohm & Haas Co.), and "DOWEX" 50 (Dow Chemical Co.). The amine may then be recovered and subsequently recycled by treatment of the resin with strong base.

The product glyoxylic acid is useful in the preparation of vanillin and ethylvanillin, as well as being used in ion exchange resins and as an acid catalyst in the pharmaceutical industry (Ullmanns). It is usually sold as a 50% (weight percent) aqueous solution. It is also to be understood that reference to glyoxylic acid in this application can also mean the glyoxylate anion, especially when the glyoxylic acid is present in a solution whose pH is greater than about 2.3.

HPLC Analysis for Glycolic, Glyoxylic, Oxalic and Formic Acid

Samples for analysis were prepared by mixing 100 μL of the reaction mixture with 300 μL of 0.1N $H_2SO_4$, then filtering the resulting solution through a Millipore Ultrafree MC filter unit (10,000 mw cutoff). Analyses for glycolic acid, glyoxylic acid, oxalic acid and formic acid were performed by high performance liquid chromatography (HPLC) on a Bio-Rad Aminex HPX-87H column (300×7.8 mm) at 40° C., using as solvent an aqueous solution of $H_2SO_4$ (0.01N) and 1-hydroxyethane-1,1-diphosphonic acid (0.1 mM) at 1.0 mL/minute. The instrument was a Waters 840 HPLC system with Model 510 pumps, a 712 WISP autosampler, and, in sequence, a 490E UV detector and 410 differential refractometer.

UV analysis was performed at 210 nm. The retention times for oxalic acid, glyoxylic acid, glycolic acid, formic acid, and propionic acid (internal standard) were 4.29, 6.09, 7.77, 8.79, and 11.41 minutes, respectively.

EXAMPLE 1

Into a 3 oz. Fischer-Porter glass aerosol reaction vessel was placed a magnetic stirring bar and 10 mL of an aqueous solution containing glycolic acid (250 mM), ethylene diamine (330 mM), FMN (0.01 mM), propionic acid (HPLC internal standard, 75 mM), glycolate oxidase (from beet leaves; 4 IU), and catalase (from *Aspergillus niger*; 14,000 IU). The final pH of this solution was 9.1. The reaction vessel was sealed and the reaction mixture was cooled to 15° C., then the vessel was flushed with oxygen by pressurizing to 70 psig (483 kPa) and venting to atmospheric pressure five times with stirring. The vessel was then pressurized to 70 psi (483 kPa) of oxygen and the mixture stirred. Aliquots (0.10 mL) were removed through a sampling port (without loss of pressure in the vessel) at regular intervals for analysis by HPLC to monitor the progress of the reaction. After 4 hours, the HPLC yields of glyoxylate, oxalate, and formate were 97.8%, 0.9%, and 0%, respectively, and 1.2% glycolate remained. The remaining activity of glycolate oxidase and catalase were 66% and 100% of their initial values, respectively.

COMPARATIVE EXAMPLE 1

The reaction in Example 1 was repeated, except that the addition of catalase was omitted. After 4 hours, the yields of glyoxylate, oxalate, and formate determined by HPLC were 6.3%, 1.1%, and 16.4%, respectively, and 7.6% glycolate remained. The remaining activity of glycolate oxidase was 15% of the initial value.

EXAMPLE 2

Into a 3 oz. Fischer-Porter glass aerosol reaction vessel was placed a magnetic stirring bar and 10 mL of an aqueous solution containing glycolic acid (750 mM), ethylene diamine (865 mM), FMN (0.01 mM), propionic acid (HPLC internal standard, 75 mM), glycolate oxidase (from spinach leaves; 10 IU), and catalase (from *Aspergillus niger*; 14,000 IU). The final pH of this solution was 9.1. The reaction vessel was sealed and the reaction mixture was cooled to 15° C., then the vessel was flushed with oxygen by pressurizing to 70 psig (483 kPa) and venting to atmospheric pressure five times with stirring. The vessel was then pressurized to 70 psi of oxygen and the mixture stirred. Aliquots (0.10 mL) were removed through a sampling port (without loss of pressure in the vessel) at regular intervals for analysis by HPLC to monitor the progress of the reaction. After 4 hours, the HPLC yields of glyoxylate, oxalate, and formate were 99.4%, 0%, and 0.2%, respectively, and 0.4% glycolate remained. The remaining activity of glycolate oxidase and catalase were 55% and 100% of their initial values, respectively.

COMPARATIVE EXAMPLE 2

The reaction in Example 2 was repeated, except that the addition of catalase was omitted. After 4 hours, the yields of glyoxylate, oxalate, and formate determined by HPLC were 0.3%, 0%, and 1.4%, respectively, and 64.3% glycolate remained. The remaining activity of glycolate oxidase was 5% of the initial value. No change in the yields of products or the amount of recovered glycolic acid was observed at longer reaction times.

EXAMPLE 3

Ruthenium metal powder

The reaction in Example 2 was repeated, except that Ruthenium metal powder (−325 mesh, 1.39 g, 14,000 IU of catalase activity) was substituted for catalase. After 22 hours, the yields of glyoxylate, oxalate, and formate were 31.3%, 0.7%, and 8.3%, respectively, and 0.5% glycolate remained. The remaining activity of glycolate oxidase was 16% of the initial activity.

EXAMPLE 4

5% Ru on $Al_2O_3$

The reaction in Example 2 was repeated, except that 5% Ru on $Al_2O_3$ (1.39 g, 14,000 IU of catalase activity) was substituted for catalase. After 22 hours, the yields of glyoxylate, oxalate, and formate were 27.6%, 0.1%, and 8.0%, respectively, and 2.3% glycolate remained. The remaining activity of glycolate oxidase was 31% of the initial activity.

EXAMPLE 5

5% Ru on Activated Carbon

The reaction in Example 2 was repeated, except that 5% Ru on activated carbon (0.615 g, 14,000 IU of catalase activity) was substituted for catalase. After 22 hours, the yields of glyoxylate, oxalate, and formate were 16.6%, 0.1%, and 0%, respectively, and 76.9% glycolate remained. The remaining activity of glycolate oxidase was <2% of the initial activity.

The reaction above was repeated, except that the 5% Ru on charcoal catalyst was soaked in a 50 mM FMN solution for 16 hours before use. After 22 hours, the yields of glyoxylate, oxalate, and formate were 32.5%, 1.0%, and 18.3%, respectively, and no glycolate remained. The remaining activity of glycolate oxidase was 17% of the initial activity.

EXAMPLE 6

$MnO_2$

The reaction in Example 2 was repeated, except that $MnO_2$ (activated, tech. grade, 0.466 g, 14,000 IU of catalase activity) was substituted for catalase. After 22 hours, the yields of glyoxylate, oxalate, and formate were 46.8%, 0.04%, and 1.0%, respectively, and 38.8% glycolate remained. After 46 hours, the yields of glyoxylate, oxalate, and formate were 60.5%, 1.2%, and 8.2%, respectively, and 1.0% glycolate remained. The remaining activity of glycolate oxidase was 19% of the initial activity.

The concentration of $MnO_2$ was lowered from 1,400 IU/mL to 350 IU/mL (0.117 g in 10 mL of reaction mixture), and the reaction repeated. After 29 hours, the yields of glyoxylate, oxalate, and formate were 44.7%, 1.5%, and 9.8%, respectively, and no glycolate remained. The remaining activity of glycolate oxidase was 38% of the initial activity.

EXAMPLE 7

50 % $MnO_2$ on Activated Carbon

The reaction in Example 2 was repeated, except that $MnO_2$ on activated carbon (0.76 g, 14,000 IU of catalase activity) was substituted for catalase; the $MnO_2$ on carbon catalyst was soaked in a 50 mM FMN solution for 16 hours before use. After 21.5 hours, the yields of glyoxylate, oxalate, and formate were 45.8%, 2.2%, and 13.1%, respectively, and no glycolate remained. The remaining activity of glycolate oxidase was 33% of the initial activity.

EXAMPLE 8

N-Methyl-N'-2-hydroxyethylimidazole-2-thione

The reaction in Example 2 was repeated, except that either 0.01 g (2.7 IU), 0.15 g (41 IU), or 1.5 g (410 IU) of N-methyl-N'-2-hydroxyethyl imidazole-2-thione was substituted for catalase. After 22 hours, the yields of glyoxylate, oxalate, and formate, as well as the recovery of unreacted glycolate, were determined by HPLC analysis. The results of these three runs are listed in the table below:

|              | Glyoxylate (%) | Oxalate (%) | Formate (%) | Glycolate (%) |
|--------------|----------------|-------------|-------------|---------------|
| 0.01 g/10 mL | 23.3           | 1.1         | 22.1        | 0             |
| 0.15 g/10 mL | 47.9           | 2.0         | 17.4        | 0             |
| 1.50 g/10 mL | 63.5           | 1.4         | 0           | 0             |

EXAMPLE 9

N,N'-Dimethyl-2-hydroxyethylimidazole-2-thione

The reaction in Example 2 was repeated, except that 1.5 g (620 IU) of N,N'-dimethyl-2-hydroxyethylimidazole-2-thione was substituted for catalase. After 21 hours, the yields of glyoxylate, oxalate, and formate were 44.6%, 0.3%, and 11.1%, respectively, and 3.3% glycolate remained. The remaining activity of glycolate oxidase was 9% of the initial activity.

EXAMPLE 10

Ferric Nitrate

The reaction in Example 2 was repeated, except that $Fe(NO_3)_3 \cdot 9H_2O$ (12.1 mg, 5.0 mmol) was substituted for catalase, and the concentration of glycolate oxidase was 6.2 IU/10 mL. After 23 hours, the yields of glyoxylate, oxalate, and formate were 24.0%, 0%, and 4.7%, respectively, and 74% glycolate remained. The remaining activity of glycolate oxidase was 25% of the initial activity.

EXAMPLE 11

Ferrocenecarboxylic Acid

The reaction in Example 2 was repeated, except that ferrocenecarboxylic acid (11.5 mg, 5.0 mmol) was substituted for catalase, and the concentration of glycolate oxidase was 6.2 IU/10 mL. After 23 hours, the yields of glyoxylate, oxalate, and formate were 9.8%, 0%, and 1.5%, respectively, and 72% glycolate remained. The remaining activity of glycolate oxidase was 19% of the initial activity.

EXAMPLE 12

Copper(II)-EDTA

The reaction in Example 2 was repeated, except that copper(II)-EDTA (copper II salt of ethylene diamine tetraacetic acid) (2.08 mM) was substituted for catalase. After 21.5 hours, the yields of glyoxylate, oxalate, and formate were 0.1%, 0.1%, and 16.3%, respectively, and 15.1% glycolate remained. The remaining activity of glycolate oxidase was <5% of the initial activity.

EXAMPLE 13

Stability of Glycolic Acid to Oxidation Catalyzed by 5% Ru on $Al_2O_3$

Into a 3 oz. Fischer-Porter glass aerosol reaction vessel was placed a magnetic stirring bar and 10 mL of an aqueous solution containing glycolic acid (750 mM), ethylene diamine (865 mM), FMN (0.01 mM), propionic acid (HPLC internal standard, 75 mM), and 5% Ru on $Al_2O_3$ (1.39 g, 14,000 IU). The final pH of this solution was 9.1. The reaction vessel was sealed and the reaction mixture was cooled to 15° C., then the vessel was flushed with oxygen by pressurizing to 70 psig (483 kPa) and venting to atmospheric pressure five times with stirring. The vessel was then pressurized to 70 psi (483 kPa) of oxygen and the mixture stirred. Aliquots (0.10 mL) were removed through a sampling port (without loss of pressure in the vessel) at regular intervals for analysis by HPLC to monitor the progress of the reaction. After 21 hours, the HPLC yields of glyoxylate, oxalate, and formate were 0.6%, 0%, and 0%, respectively, and 97% glycolate remained.

EXAMPLE 14

Stability of Glyoxylic Acid to Oxidation Catalyzed by $MnO_2$

Into a 3 oz. Fischer-Porter glass aerosol reaction vessel was placed a magnetic stirring bar and 10 mL of an aqueous solution containing glyoxylic acid (750 mM), ethylene diamine (865 mM), FMN (0.01 mM), propionic acid (HPLC internal standard, 75 mM), and $MnO_2$ (0.466 g, 14,000 IU). The final pH of this solution was 9.1. The reaction vessel was sealed and the reaction mixture was cooled to 15° C., then the vessel was flushed with oxygen by pressurizing to 70 psig (483 kPa) and venting to atmospheric pressure five times with stirring. The vessel was then pressurized to 70 psi (483 kPa) of oxygen and the mixture stirred. Aliquots (0.10 mL) were removed through a sampling port (without loss of pressure in the vessel) at regular intervals for analysis by HPLC to monitor the process of the reaction. After 21.5 hours, the HPLC yields of glyoxylate, oxalate, and formate were 14.9%, 2.6%, and 50%, respectively.

Having thus described and exemplified the invention with a certain degree of particularlity, it should be appreciated that the following claims are not to be so limited but are to be afforded a scope commensurate with the wording of each element of the claim and equivalents thereof.

We claim:

1. A process for the production of glyoxylic acid comprising contacting, in aqueous solution, at a pH of about 7 to about 10 and a temperature of 0° to 40° C., glycolic acid, glycolate oxidase, and oxygen and from 25 to 100,000 IU/mL of a non-enzymatic catalyst for decomposing hydrogen peroxide formed in said process wherein the initial concentration of glycolic acid is 200 mM to about 2500 mM and of glycolate oxidase is 0.01 to 100 IU/mL, wherein the ratio, as measured in IU/mL, for each of peroxide-decomposing catalyst to glycolate oxidase is at least about 250:1, and an amine buffer capable of forming a chemical adduct with glyoxylic acid where the initial molar ratio of amine to glycolic acid is within the range of from 1.0 to 3.0.

2. The process of claim 1 wherein the non-enzymatic catalyst for the decomposition of hydrogen peroxide is unsupported manganese (IV) oxide, manganese oxide (IV) on carbon, ruthenium metal powder, ruthenium metal on alumina, ruthenium metal on carbon, platinum oxide, platinum black, platinum on alumina, palladium black, palladium on alumina, copper(II) oxide, lead on alumina, soluble salts or chelates or Mn(II), Mn(IV), Cu(II), Ni(II), Co(II), Zn(II), Fe(II), Fe(III), Cr(III), activated carbon or N,N'-di(lower alkyl-, or hydroxy-substituted lower alkyl-substituted imidazole-2-thiones.

3. The process of claim 2 wherein from about 0.1 to about 4 IU/mL of glycolate oxidase is present in the reaction medium.

4. The process of claim 3 wherein the oxygen pressure is from 1 to 50 atmospheres.

5. The process of claim 4 wherein from 350 to 14,000 IU/mL of the hydrogen peroxide decomposition catalyst is present.

6. The process of claim 5 wherein the oxygen pressure is from 1 to 15 atmospheres.

7. The process of claim 6 wherein the temperature is from 5° to 15° C.

8. The process of claim 7 wherein the amine buffer is ethylene diamine, tris(hydroxymethyl) methylamine, piperazine, glyclyglycine, or mixtures thereof.

9. The process of claim 8 wherein the hydrogen peroxide decomposition catalyst is ruthenium metal powder.

10. The process of claim 8 wherein the hydrogen peroxide decomposition catalyst is ruthenium on alumina.

11. The process of claim 8 wherein the hydrogen peroxide decomposition catalyst is ruthenium on activated carbon.

12. The process of claim 8 wherein the hydrogen peroxide decomposition catalyst is manganeses oxide.

13. The process of claim 8 wherein the hydrogen peroxide decomposition catalyst is manganese oxide on activated carbon.

14. The process of claim 8 wherein the hydrogen peroxide decomposition catalyst is N-methyl-N'-2-hydroxyethylimidazole-2-thione.

15. The process of claim 8 wherein the hydrogen peroxide decomposition catalyst is N,N-dimethyl-2-hydroxyethylimidazole-2-thione.

16. The process of claim 8 wherein the hydrogen peroxide decomposition catalyst is ferric nitrate.

17. The process of claim 8 wherein the hydrogen peroxide decomposition catalyst is ferrocenecarboxylic acid.

18. The process of claim 1 wherein the amine buffer is ethylene diamine.

19. The process of claim 1 wherein the amine buffer is tris(hydroxymethyl)methylamine.

20. The process of claim 1 wherein the amine buffer is piperazine.

21. The process of claim 1 wherein the amine buffer is glyclyglycine.

* * * * *